(12) United States Patent
Ko et al.

(10) Patent No.: US 10,751,472 B2
(45) Date of Patent: Aug. 25, 2020

(54) DRUG INJECTING IMPLEMENT EQUIPPED WITH SLIDING ATTACHMENT UNIT

(71) Applicant: KOREA INSTITUTE OF INDUSTRIAL TECHNOLOGY, Cheonan-si, Chungcheongnam-do (KR)

(72) Inventors: Cheol Woong Ko, Yongin-si (KR); Keyoung Jin Chun, Uiwang-si (KR); Sang Kuy Han, Yongin-si (KR); In Hoon Jang, Suwon-si (KR)

(73) Assignee: KOREA INSTITUTE OF INDUSTRIAL TECHNOLOGY, Chungcheongnam-Do (KR)

( * ) Notice: Subject to any disclaimer, the term of this patent is extended or adjusted under 35 U.S.C. 154(b) by 304 days.

(21) Appl. No.: 15/537,767

(22) PCT Filed: Jul. 27, 2015

(86) PCT No.: PCT/KR2015/007818
§ 371 (c)(1),
(2) Date: Jun. 19, 2017

(87) PCT Pub. No.: WO2016/098983
PCT Pub. Date: Jun. 23, 2016

(65) Prior Publication Data
US 2018/0272068 A1  Sep. 27, 2018

(30) Foreign Application Priority Data

Dec. 19, 2014  (KR) .......................... 10-2014-0184352

(51) Int. Cl.
*A61M 5/24* (2006.01)
*A61M 5/46* (2006.01)
(Continued)

(52) U.S. Cl.
CPC ............ *A61M 5/24* (2013.01); *A61B 1/00052* (2013.01); *A61B 1/015* (2013.01); *A61B 1/042* (2013.01);
(Continued)

(58) Field of Classification Search
CPC ............ A61B 5/0084; A61B 1/00; A61B 1/04; A61B 1/05; A61B 1/00052; A61B 1/015;
(Continued)

(56) References Cited

U.S. PATENT DOCUMENTS 4,153,356 A * 5/1979 Hama .................. A61B 1/0669
396/159
4,191,187 A * 3/1980 Wright ................ A61M 5/1456
128/DIG. 1
(Continued)

FOREIGN PATENT DOCUMENTS

DE  19618963 A1 * 11/1997 ............. A61B 1/043
JP  2011152305 A * 8/2011
(Continued)

*Primary Examiner* — Jason E Flick
*Assistant Examiner* — Mark A Igel
(74) *Attorney, Agent, or Firm* — Cantor Colburn LLP (57) ABSTRACT

A drug injecting implement equipped with a sliding attachment unit includes a main body having an accommodating space formed on the inside thereof, and equipped with a handle, an insertion needle having a solution flow pathway for a drug solution to flow therethrough, and of which one side is secured inside the main body while the other side extends outside the main body, an image measuring unit disposed on the main body, and of which one portion is formed in elongated fashion, a sliding attachment unit having an open topped accommodating unit for accommodating a separate drug container on the inside thereof, and which slides selectively on the side surface of the main body and a solution injecting unit provided on the main body and (Continued)

which is adapted such that the drug solution accommodated inside the drug container is injected into the human body via the insertion needle.

10 Claims, 6 Drawing Sheets

(51) Int. Cl.
| | | |
|---|---|---|
| *A61M 5/145* | (2006.01) | |
| *A61B 1/00* | (2006.01) | |
| *A61B 1/015* | (2006.01) | |
| *A61B 1/04* | (2006.01) | |
| *A61B 1/06* | (2006.01) | |
| *A61B 1/07* | (2006.01) | |
| *A61B 17/34* | (2006.01) | |
| *A61M 5/31* | (2006.01) | |
| *A61M 5/315* | (2006.01) | |
| *A61M 5/172* | (2006.01) | |
| *A61B 34/20* | (2016.01) | |
| *A61B 90/30* | (2016.01) | |
| *A61B 90/00* | (2016.01) | |

(52) U.S. Cl.
CPC .............. *A61B 1/0669* (2013.01); *A61B 1/07* (2013.01); *A61B 34/20* (2016.02); *A61M 5/145* (2013.01); *A61M 5/1456* (2013.01); *A61M 5/1458* (2013.01); *A61M 5/172* (2013.01); *A61M 5/2422* (2013.01); *A61M 5/31566* (2013.01); *A61M 5/46* (2013.01); *A61B 1/00078* (2013.01); *A61B 17/3403* (2013.01); *A61B 17/3468* (2013.01); *A61B 2034/2057* (2016.02); *A61B 2090/306* (2016.02); *A61B 2090/3614* (2016.02); *A61B 2090/372* (2016.02); *A61M 2005/2414* (2013.01); *A61M 2005/2433* (2013.01); *A61M 2005/3125* (2013.01); *A61M 2205/3306* (2013.01); *A61M 2205/583* (2013.01); *A61M 2205/587* (2013.01)

(58) Field of Classification Search
CPC ......... A61B 1/042; A61B 1/0669; A61B 1/07; A61B 1/00078; A61B 34/20; A61B 2034/2057; A61B 2090/306; A61B 2090/3614; A61B 2090/372; A61B 17/3468; A61M 5/145; A61M 5/1456; A61M 5/1458; A61M 5/172; A61M 5/2422; A61M 5/31566; A61M 5/46; A61M 2005/2414; A61M 2005/2433; A61M 2005/3125; A61M 2205/3306; A61M 2205/583; A61M 2205/587; A61M 5/24

See application file for complete search history.

(56) References Cited

U.S. PATENT DOCUMENTS

| | | | | |
|---|---|---|---|---|
| 4,349,255 A * | 9/1982 | Takayama | ............. | G01J 1/1626 396/159 |
| 4,417,889 A * | 11/1983 | Choi | ................ | A61M 5/14546 604/246 |
| 4,424,720 A * | 1/1984 | Bucchianeri | ........ | A61M 5/1456 128/DIG. 1 |
| 4,529,401 A * | 7/1985 | Leslie | ................ | A61M 5/1456 128/DIG. 1 |
| 5,034,003 A * | 7/1991 | Denance | ................ | A61M 5/20 604/117 |
| 5,176,502 A * | 1/1993 | Sanderson | .......... | A61M 5/1456 417/18 |
| 5,318,522 A * | 6/1994 | D'Antonio | .......... | A61M 5/2425 604/135 |
| 5,505,709 A * | 4/1996 | Funderburk | ........ | A61M 5/1456 604/151 |
| 5,578,014 A * | 11/1996 | Erez | .......................... | A61F 7/10 604/192 |
| 5,925,018 A * | 7/1999 | Ungerstedt | ......... | A61M 5/1456 604/155 |
| 5,954,697 A * | 9/1999 | Srisathapat | ......... | A61M 5/1456 604/154 |
| 5,984,894 A * | 11/1999 | Poulsen | .............. | A61M 5/1413 604/151 |
| 5,993,378 A * | 11/1999 | Lemelson | .......... | A61B 1/00096 600/109 |
| 5,999,844 A * | 12/1999 | Gombrich | ............ | A61B 5/0071 600/109 |
| 6,213,354 B1 * | 4/2001 | Kay | ................... | A61M 5/16804 222/14 |
| 6,293,911 B1 * | 9/2001 | Imaizumi | ........... | A61B 1/00009 600/160 |
| 6,302,855 B1 * | 10/2001 | Lav | .................... | A61B 5/14532 600/584 |
| 6,796,964 B2 * | 9/2004 | Eidson | ..................... | A61D 7/00 604/135 |
| 6,932,242 B2 * | 8/2005 | Gerlach | ................ | A61M 5/142 222/113 |
| 7,625,354 B2 * | 12/2009 | Hochman | .......... | A61M 5/1456 137/68.11 |
| 7,806,868 B2 * | 10/2010 | De Polo | .............. | A61M 5/1456 604/131 |
| 7,918,825 B2 * | 4/2011 | O'Connor | ......... | A61M 5/14248 604/151 |
| 7,963,433 B2 * | 6/2011 | Whitman | .......... | A61B 17/07207 227/178.1 |
| 7,967,795 B1 * | 6/2011 | Cabiri | ............... | A61M 5/14566 604/154 |
| 8,262,616 B2 * | 9/2012 | Grant | ................ | A61M 5/14244 604/151 |
| 8,323,262 B2 * | 12/2012 | D'Alessio | ........ | A61B 17/00491 604/520 |
| 8,529,520 B2 * | 9/2013 | Daniel | .................... | A61M 5/20 604/207 |
| 8,545,440 B2 * | 10/2013 | Patrick | ..................... | A61B 8/00 604/131 |
| 8,926,334 B2 * | 1/2015 | Park | ..................... | G09B 23/285 434/262 |
| 2002/0077588 A1 * | 6/2002 | Schneider | .............. | A61M 5/007 604/82 |
| 2002/0077601 A1 * | 6/2002 | Kawagishi | ............... | A61M 5/20 604/224 |
| 2002/0103420 A1 * | 8/2002 | Coleman | ............ | A61B 1/00087 600/173 |
| 2004/0030219 A1 * | 2/2004 | Kim | .................... | A61B 1/00039 600/101 |
| 2004/0135078 A1 * | 7/2004 | Mandro | ................ | A61M 5/145 250/231.13 |
| 2005/0154354 A1 * | 7/2005 | Kawasaki | ........... | A61M 5/1785 604/232 |
| 2005/0238507 A1 * | 10/2005 | Dilanni | ............. | A61M 5/14244 417/415 |
| 2008/0033290 A1 * | 2/2008 | Saadat | ............... | A61B 1/00089 600/433 |
| 2008/0033569 A1 * | 2/2008 | Ferren | ..................... | A61B 34/20 623/23.7 |
| 2008/0058650 A1 * | 3/2008 | Saadat | ............... | A61M 25/1002 600/478 |
| 2008/0103564 A1 * | 5/2008 | Burkinshaw | ..... | A61B 17/00491 607/96 |
| 2008/0132763 A1 * | 6/2008 | Isaacson | ............ | A61B 1/015 600/158 |
| 2008/0142554 A1 * | 6/2008 | Lafferty | ................ | A61M 5/001 222/566 |
| 2017/0224935 A1 * | 8/2017 | Hoffmann | ................ | A61M 5/20 |

(56) References Cited

U.S. PATENT DOCUMENTS

FOREIGN PATENT DOCUMENTS

| | | | |
|---|---|---|---|
| JP | 2011152305 A | 8/2011 | |
| KR | 1020040084768 A | 10/2004 | |
| KR | 1020090131724 A | 12/2009 | |
| KR | 101129809 B1 * | 3/2012 | |
| KR | 101129809 B1 | 3/2012 | |
| KR | 20150046960 A * | 5/2015 | |
| KR | 20150048030 A * | 5/2015 | |
| WO | WO-2015060545 A1 * | 4/2015 | ......... A61B 1/00066 |

* cited by examiner

DRUG INJECTING IMPLEMENT EQUIPPED WITH SLIDING ATTACHMENT UNIT

TECHNICAL FIELD

The present invention relates to a drug injecting implement equipped with a sliding attachment unit, and more particularly, to a drug injecting implement equipped with a sliding attachment unit capable of injecting a drug by applying a universal drug container or cartridge.

BACKGROUND ART

Generally, an injection is a medical procedure for injecting a drug into a tissue or blood vessel of a living body by using a syringe so as to prevent and treat various diseases. It is one of the effective treatment methods that has advantages such as the high efficacy in comparison with an internal application or an external application in the administration of medicines, the availability of the high concentration drug, and the ability to administer medicines to a patient who cannot use internal medicine.

Examples of such injections include an intradermal injection injected between the epidermis and the dermis of the skin, a subcutaneous injection injected into the subcutaneous tissue, a muscle injection injected into the muscle deep in the skin, an intravenous injection injected directly into the vein, and the like. Usually, the injection of drug solution is accomplished by directly handling a syringe.

Particularly, in a related art, a drug injecting implement equipped with a sliding attachment unit has been used in such a manner that a practitioner directly injects a needle into a patient's body to administer the drug solution.

However, since the conventional drug injecting implement equipped with a sliding attachment unit does not have a means for indicating the position of an insertion needle in the human body, the injection is accomplished for the injection part on the human body only by the eye. As a result, the practitioner adjusts the injection position of the drug solution through a pure sense or a guess, which makes it difficult to control the exact administration position of the drug solution.

Thus, it is difficult to precisely measure the injection site on the human body to which the injection needle is inserted during the procedure, so that the accuracy of the procedure may be lowered. Accordingly, when accurate operation is required, an expensive drug may be wasted or the efficacy may be lowered. Furthermore, the inconvenience of re-injection may occur.

In addition, in the case of a drug injecting implement equipped with a general sliding attachment unit, it is necessary to use a separately prepared drug container suitable for a corresponding drug injecting implement, so that it is difficult to control the drug dose according to the user's convenience.

Accordingly, there is an inconvenience in that the drug injections should be performed more than once when the capacity of the drug container is smaller than the dose.

DISCLOSURE

Technical Problem

The present invention has been made in view of the above problems, and provides a drug injecting implement equipped with a sliding attachment unit capable of accurately adjusting a drug injection position by inserting an image measuring unit together with an insertion needle into a human body, and easily coupling a universal drug container or cartridge through a separate sliding attachment unit.

Technical Solution

In an aspect, there is provided a drug injecting implement equipped with a sliding attachment unit, the implement including: a main body which has an accommodating space formed on the inside thereof, and is equipped with a handle to be gripped by a user; an insertion needle in which is formed a solution flow pathway for a drug solution to flow therethrough, and of which one side is secured inside the main body while the other side extends outside the main body so as to be inserted into a human body; an image measuring unit which is disposed on the main body, and of which one portion is formed in elongated fashion so as to be inserted into the human body together with the insertion needle so as to capture an image; a sliding attachment unit which has an open topped accommodating unit for accommodating a separate drug container on the inside thereof, and which slides selectively on the side surface of the main body so as to position the drug container inside the accommodating space; and a solution injecting unit which is provided on the main body and is adapted such that the drug solution accommodated inside the drug container is injected into the human body via the insertion needle due to the action of a user.

The drug container is provided with a discharge port through which the drug solution is discharged and which is disposed in one side of the drug container, wherein the main body is provided with a communication nozzle which allows the discharge port to communicate with the insertion needle when the drug container is positioned in the accommodating space by the sliding attachment unit.

The sliding attachment unit further includes a sliding guide which is formed on an outer surface of the sliding attachment unit so as to be slidable in a lateral direction without being detached from the main body.

The accommodating unit further includes a fixing means which surrounds a part of the side surface of the drug container to prevent the drug container from moving unintentionally inside the accommodating unit.

The solution injecting unit includes: a rotating shaft which is elongated in a front and rear direction in the main body and which has a screw thread formed on an outer surface of the rotating shaft, and which selectively rotates according to the action of a user; and a pressing member which is penetrated by the rotating shaft and which is fitted to the screw thread, and which slides forward and backward in the main body due to a rotation of the rotating shaft to discharge the drug accommodated in the drug container.

The solution injecting unit further includes a driving motor which is connected to the rotating shaft and which provides a rotational force to the rotating shaft by a separate operating means.

The image measuring unit includes: a light source which is provided in the main body to emit light; a photographing unit which is elongated and is disposed inside the insertion needle, and which receives the light emitted from the light source and photographs an internal image of human body; and a display unit which is provided outside the main body and which displays the image photographed by the photographing unit to a user.

The photographing unit includes a light emitting line which is connected to the light source and which emits light in the inside of the human body and a photographing line which photographs an internal image of human body to transmit to the display unit.

The light emitting line and the photographing line are provided with an optical fiber.

Advantageous Effects

A drug injecting implement equipped with a universally applicable sliding attachment unit according to the present invention has the following effects.

First, a drug container or a cartridge which slides along the lateral direction and which is commonly used may be selectively coupled with a main body and may discharge a drug accommodated in the drug container or the cartridge due to the action of a user, thereby injecting the drug into the patient's body through an insertion needle regardless of the size of the drug container or the cartridge.

Second, a part of a separate image measuring unit is inserted together with the insertion needle inserted into the human body such that the user can precisely adjust the position of the injection needle, thereby accurately adjusting the injection position of the drug.

The effects of the present invention are not limited to the effects mentioned above, and other effects not mentioned can be clearly understood by those skilled in the art from the description of the claims.

MODE FOR INVENTION

Hereinafter, preferred embodiments of the present invention will be described with reference to the accompanying drawings. In describing the present embodiment, the same designations and the same reference numerals are used for the same components, and further description thereof will be omitted.

First, a drug injecting implement equipped with a sliding attachment unit according to an embodiment of the present invention will be described with reference to FIGS. 1 to 5.

Figure 1:
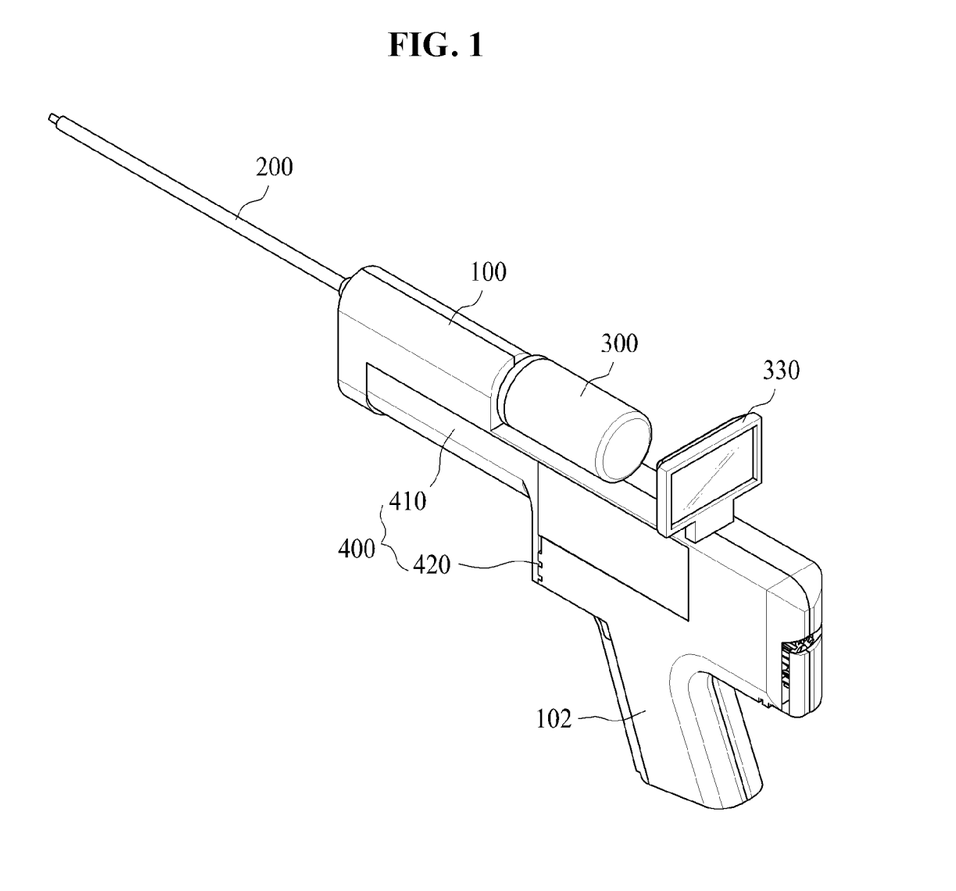
FIG. 1 is a perspective view schematically showing a configuration of a drug injecting implement equipped with a sliding attachment unit according to an embodiment of the present invention.
Figure 2:
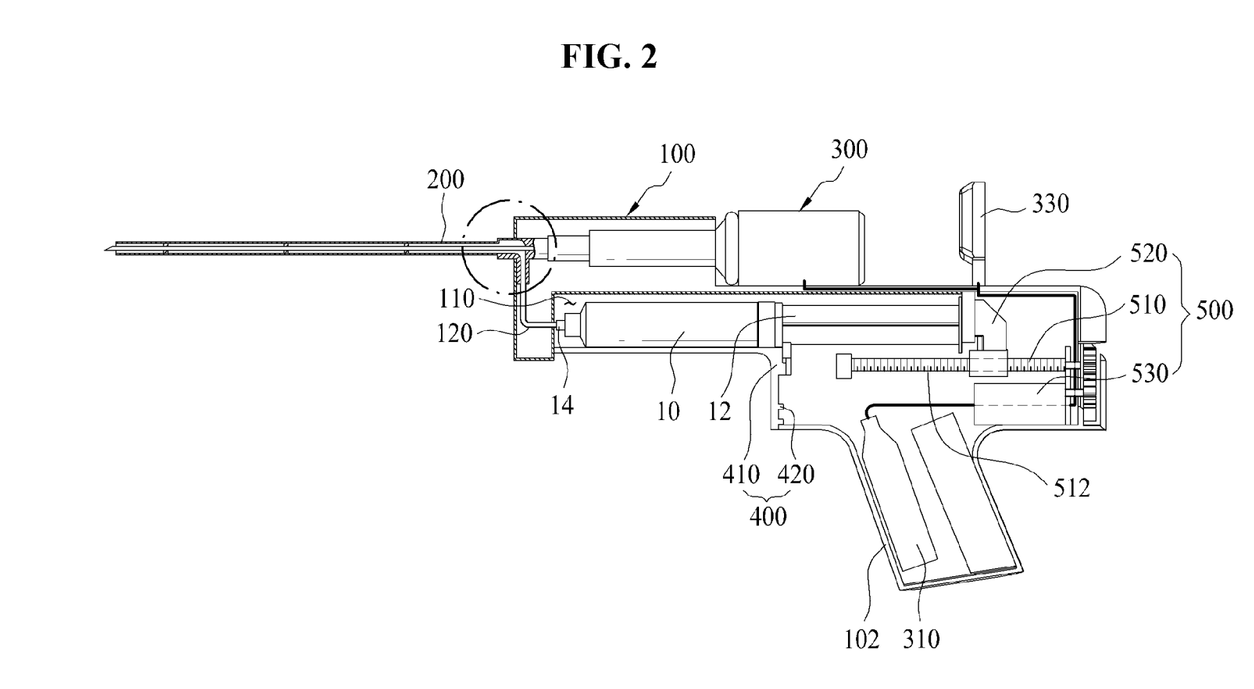
FIG. 2 is a sectional view showing an internal configuration of the drug injecting implement equipped with a sliding attachment unit of FIG. 1.
Figure 3:
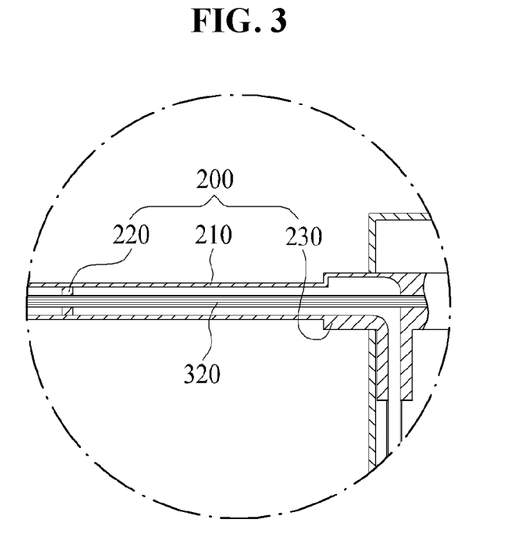
FIG. 3 is an enlarged view of the internal configuration of the drug injecting implement of FIG. 2.

FIG. 1 is a perspective view schematically showing a configuration of a drug injecting implement equipped with a sliding attachment unit according to an embodiment of the present invention, FIG. 2 is a sectional view showing an internal configuration of the drug injecting implement equipped with a sliding attachment unit of FIG. 1, and FIG. 3 is an enlarged view of the internal configuration of the drug injecting implement of FIG. 2.

Figure 4:
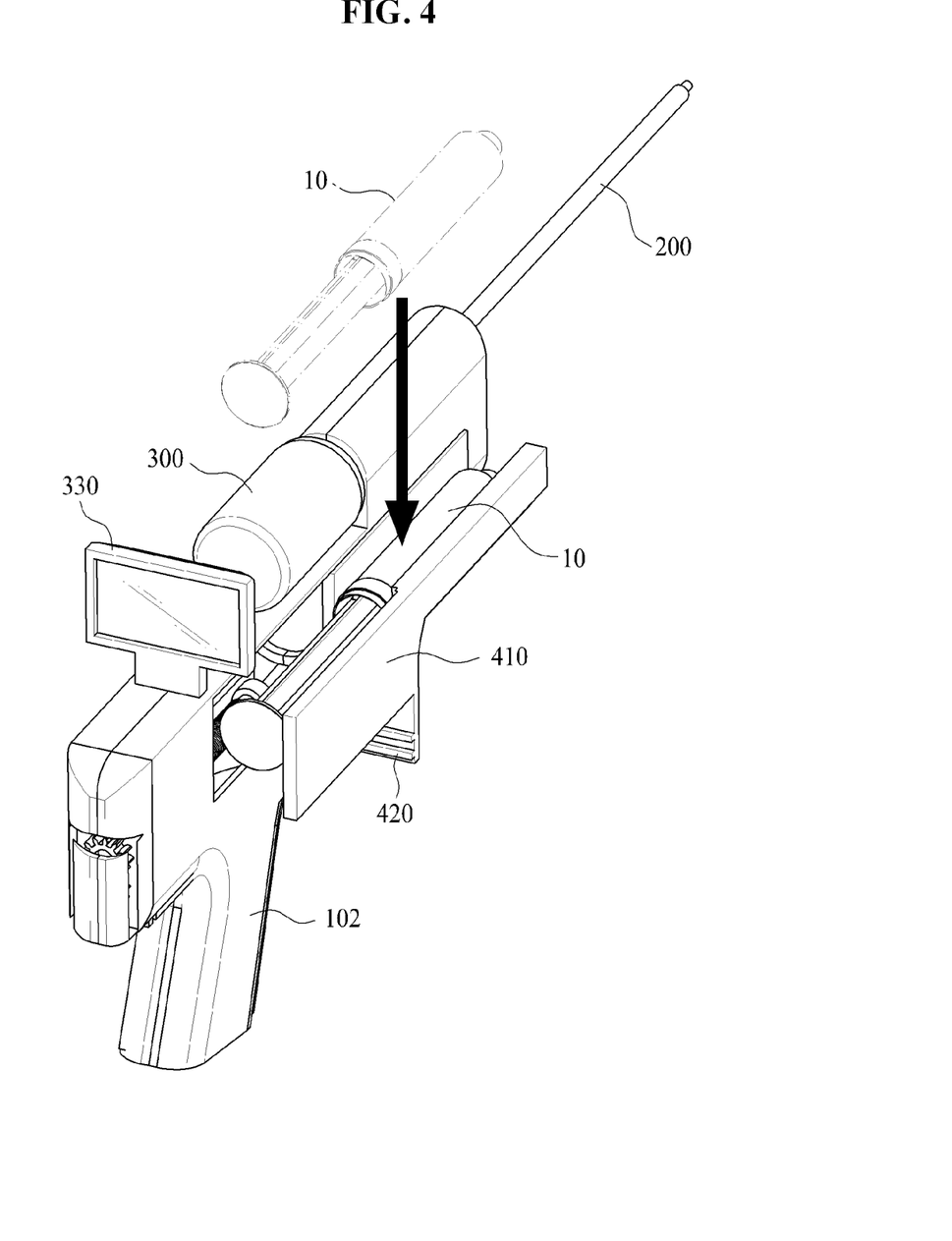
FIG. 4 is a view showing a state in which a drug container and a sliding attachment unit are coupled in the drug injecting implement equipped with a sliding attachment unit of FIG. 1.
Figure 5:
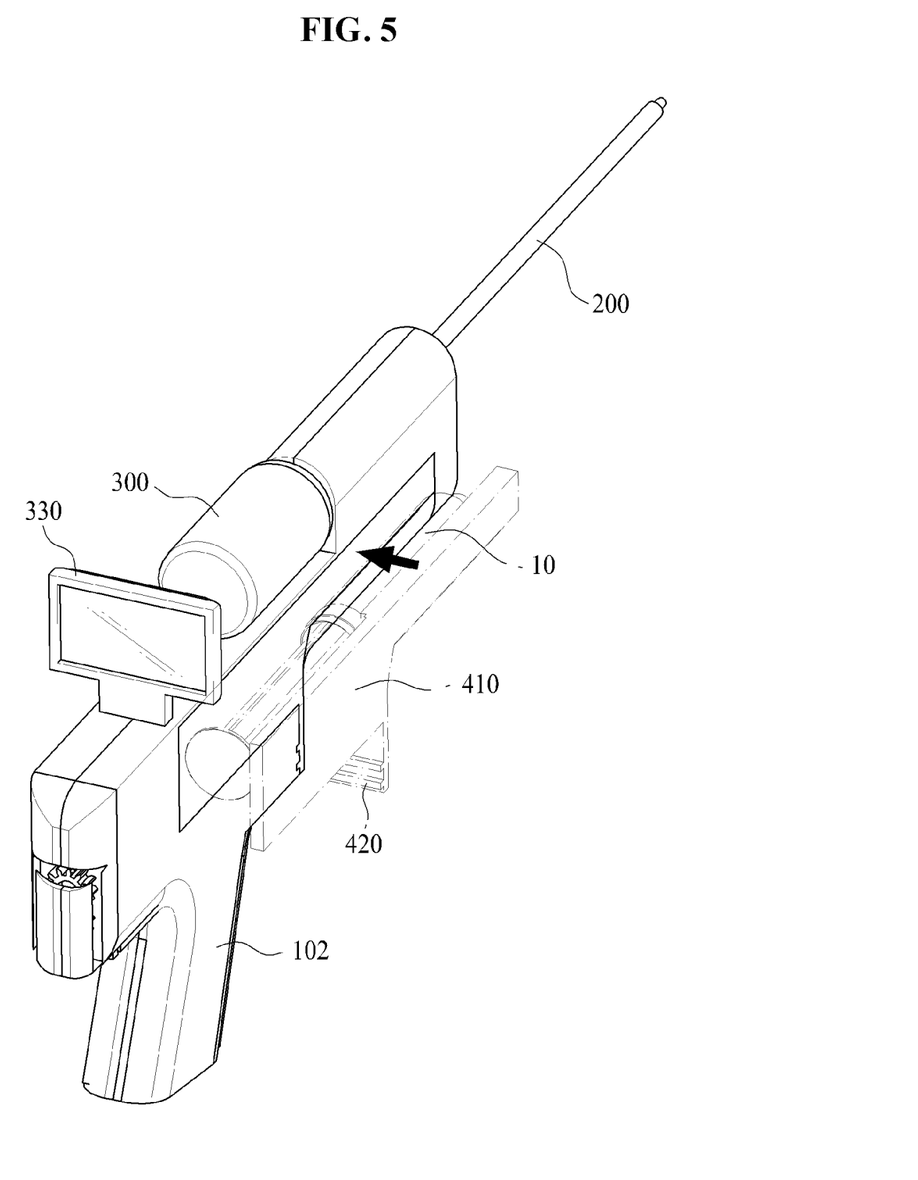
FIG. 5 is a view illustrating a state in which the sliding attachment unit of FIG. 4 is inserted into a main body while being coupled with the drug container.

In addition, FIG. 4 is a view showing a state in which a drug container and a sliding attachment unit are coupled in the drug injecting implement equipped with a sliding attachment unit of FIG. 1, and FIG. 5 is a view illustrating a state in which the sliding attachment unit of FIG. 4 is inserted into a main body while being coupled with the drug container.

The drug injecting implement equipped with the sliding attachment unit according to the present invention is an apparatus for inserting a drug into the inner parts of human body by inserting an insertion needle 200 into a human body, which inserts a drug accommodated in a widely used drug container 10 or a cartridge into the human body while the drug container 10 or the cartridge is coupled to the drug injecting implement.

The drug injecting implement equipped with a sliding attachment unit according to the present invention mainly includes a main body 100, the insertion needle 200, an image measuring unit 300, a sliding attachment unit 400, and a solution injecting unit 500.

The main body 100 supports a whole apparatus, and a user grips and manipulates the main body 100. This configuration includes the insertion needle 200, the image measuring unit 300, the sliding attachment unit 400, and the solution injecting unit 500. The user grips this configuration to inject the drug into the human body.

Specifically, the main body 100 is elongated in the front-rear direction, and a handle 102 is provided at a lower portion so that the user may grip the handle.

In addition, the main body 100 has an accommodating space 110 formed therein so that the universal drug container 10 or the cartridge can be selectively accommodated by the sliding attachment unit 400. Here, the main body 100 is partially opened to communicate with the accommodating space 110, and the opening and closing of the accommodating space 110 is selectively controlled by the sliding attachment unit 400 described later.

In addition, the main body 100 is provided with the image measuring unit 300 such that a part of the image measuring unit can be inserted into the human body together with the insertion needle 200 described later, and the user can directly check the position of an end portion of the insertion needle 200 by using the image measuring unit 300.

Here, the drug container 10 may be formed of a generally used syringe, cartridge, or the like, and the drug may be received therein and selectively discharged to the outside.

Hereinafter, in the present embodiment, the drug container 10 is described in the form of a syringe.

In the present embodiment, the drug container 10 is implemented in the form of a syringe to form a discharge port 14 through which the drug is discharged forward and a piston 12 which is provided in the opposite side of the discharge port 14 so that the drug can be discharged to the discharge port 14 through the sliding of the piston 12.

Thus, the drug container 10 is implemented to be long in the form of a syringe and is coupled to the main body 100.

In the present embodiment, the main body 100 is provided with the handle 102 to be gripped by the user at a lower portion, and an opening is formed on the side surface of the main body 100 so that the sliding attachment unit 400 may be coupled and accommodated in the inside of the accommodating space 110.

Meanwhile, the insertion needle 200 has a solution flow pathway through which the drug solution flows, and one side of the insertion needle 200 is fixed to the main body 100 and the other side of the insertion needle 200 is extended to the front of the main body 100 to be protruded.

Specifically, the insertion needle 200 according to the present invention includes a solution injecting unit 210 which is formed in an elongated shape and which has a solution flow pathway formed therein along the longitudinal direction and which injects the drug solution delivered from the drug container 10 into the human body, and a guide unit 220 which is provided in the solution injecting unit 210 and to which the image measuring unit 300 described later is fixed.

In the present embodiment, the solution injecting unit 210 is formed in a cylindrical thin tube shape, and the other end of the solution injecting unit 210 is formed to be inserted into the user's body. The guide unit 220 is formed to fix a part of the image measuring unit 300 which is disposed inside the solution injecting unit 210.

At this time, a plurality of guide units 220 may be provided along the longitudinal direction of the solution injecting unit 210, and each of the guide units 220 may be radially formed to fix the image measuring unit 300.

Unlike the present embodiment, the guide unit 220 may have various shapes such as a long cylindrical shape or may be formed of a single member. Further, any shape can be applied as long as it is possible to fix a part of the image measuring unit 300 in the solution injecting unit 210.

Meanwhile, the insertion needle 200 is provided with a separate adapter 230 at one side thereof and the adapter 230 is positioned inside the main body 100 so that the drug container 10 and the solution injecting unit 210 can communicate with each other and a part of the image measuring unit 300 can be inserted into the solution injecting unit 210.

Thus, the other side of the insertion needle 200 is inserted into the human body of the user, and one side of the insertion needle 200 is fixed to the main body 100 and is provided with the adapter 230 in the end portion of the insertion needle 200 so that a part of the image measuring unit 300 described later can be inserted.

In addition, the adapter 230 is configured to communicate with the drug container 10 so that the drug solution accommodated in the drug container 10 can be injected into the human body via the insertion needle 200.

Meanwhile, the image measuring unit 300 is disposed in the main body 100 and is partly elongated, inserted into the human body together with the insertion needle 200, and captures an image of the inside of the human body. The image measuring unit 300 mainly includes a light source 310, a photographing unit 320, and a display unit 330.

The light source 310 is provided in the main body 100 to emit light, and a general light emitting device can be applied.

In the present embodiment, the light source 310 may be provided inside the handle 102 as shown in the drawing, or may be separately provided in the outside of the main body 100.

Meanwhile, the photographing unit 320 is formed to be long and is formed of a plurality of optical fibers, and is partially connected to the light source 310 and positioned inside the solution injecting unit 210 through the adapter 230.

In addition, the photographing unit 320 receives light emitted from the light source 310 and photographs an internal image in the state in which it is inserted into the human body together with the insertion needle 200.

That is, the photographing unit 320 is formed to be long, and photographs the position of the end portion of the other side of the insertion needle 200 through the light transmitted from the light source 310 while one side of the photographing unit 320 is connected to the light source 310 and the other side of the photographing unit 320 is inserted into the human body together with the insertion needle 200.

In addition, the display unit 330 is a configuration which is provided outside the main body 100 and which displays an image photographed by the separate photographing unit 320 to a user, and is connected to one end of the photographing unit 320.

At this time, the display unit 330 includes a general liquid crystal display (LCD) apparatus so that a user can directly check an end portion image of the insertion needle 200 in real time.

As described above, the image measuring unit 300 according to the present invention may be configured in such a manner that the photographing unit 320 is composed of a plurality of optical fibers and one side of the photographing unit 320 is dividedly connected to the light source 310 and the display unit 330, and transmits the image of the inside of the human body to the display unit 330 through the light generated from the light source 310.

In the image measuring unit 300 of the present embodiment, as shown in the drawing, one side of the photographing unit 320 is branched and connected to the light source 310 which is provided inside the handle 102 and the display unit 330 which is provided outside the main body 100, so that a user can check the image of the end portion of the insertion needle 200 in real time.

A detailed configuration of the photographing unit 320 will be described later with reference to FIG. 6.

Meanwhile, the sliding attachment unit 400 is provided with an accommodating unit 410 which has an upper portion opened to accommodate the drug container 10 and which selectively slides on the side surface of the main body 100 so that the drug container 10 can be positioned inside the accommodating space 110.

Specifically, the sliding attachment unit 400 includes the accommodating unit 410 which has an open upper portion so that the drug container 10 can be selectively mounted, and a sliding guide 420 which is formed on an outer surface of the accommodating unit 410 so as to be slidable in a lateral direction without being detached from the main body 100.

The accommodating unit 410 has an opened upper portion and is elongated to correspond to the shape of the drug container 10, and the drug container 10 is selectively accommodated or discharged by the user.

Although not shown, the accommodating unit 410 further includes a fixing means (not shown) which surrounds at least a part of the side surface of the drug container 10 and prevents the drug container 10 from moving unintentionally inside the accommodating unit 410.

In this case, the fixing means may be configured to surround an upper portion of the drug container 10 in a state where the drug container 10 is seated inside the accommodating unit 410. On the other hand, the fixing means may be provided in a lower portion of the drug container 10 so that the drug container 10 can be fixed through interference fit.

In the present embodiment, the accommodating unit 410 is formed to be long and is provided with an open upper surface and open front and rear sides, and a side surface is formed so that the drug container 10 can be accommodated.

As shown in FIG. 5, the above described accommodating unit 410 may be slid on the side surface of the main body 100 so that the drug container 10 can be positioned inside the accommodating space 110.

Here, when the drug container 10 is slid by the accommodating unit 410 and is positioned in the accommodating space 110, the discharge port 14 formed in the drug container 10 and the insertion needle 200 should be communicated.

Accordingly, the main body 100 has a separate communication nozzle 120 for allowing the discharge port 14 and the insertion needle 200 to communicate with each other when the drug container 10 is positioned inside the accommodating space 110.

The communication nozzle 120 is formed in a general nozzle shape so that one side is connected to the adapter 230 and the other side is connected to the discharge port 14, and can be selectively separated from the discharge port 14 according to a sliding state of the accommodating unit 410.

Accordingly, even if the drug container 10 accommodated in the accommodating unit 410 slides on the side surface of the main body 100 and is inserted into the accommodating space 110, the drug solution can be stably injected into the human body via the insertion needle 200.

Meanwhile, the sliding guide 420 is formed on the outer surface of the accommodating unit 410 and is configured to be slidable in the lateral direction without detaching from the main body 100.

In detail, as shown in FIG. 2, the sliding guide 420 is formed in a protruding shape at a portion where the main body 100 and the accommodating unit 410 slide, so that they can be engaged with each other and the accommodating unit 410 can slide to the side surface of the main body 100.

At this time, the sliding guide 420 is not completely separated from the main body 100 when sliding on the side surface of the main body 100.

Thus, the accommodating unit 410 can be selectively slid along the transverse direction on the main body 100 due to the sliding guide 420 and the position of the accommodating unit 410 can be adjusted, and the accommodating space 110 may be selectively closed according to the sliding state of the accommodating unit 410.

In the present embodiment, the sliding guide 420 is formed in the rear side of the accommodating unit 410 so as to be slidable with respect to the main body 100. Alternatively, the sliding guide 420 may be formed in various positions.

Since the sliding attachment unit 400 is configured as described above, the drug container 10 can be stably accommodated in the accommodating space 110. In addition, since the drug container 10 is fixed to the accommodating unit 410, the discharge port 14 formed in the drug container 10 can be positioned at a certain position in the accommodating space 110 to achieve a communication with the communication nozzle 120.

A process of inserting the drug container 10 into the accommodating space 110 by the sliding attachment unit 400 will be described below.

Firstly, as shown in FIG. 4, the drug container 10 containing the drug solution is mounted inside the accommodating unit 410 while the accommodating unit 410 is exposed to the side surface of the main body 100 and the upper portion is opened.

At this time, as described above, the drug container 10 is stably fixed to a preset position on the accommodating unit 410 by the fixing means.

In addition, as shown in FIG. 5, the user presses the accommodating unit 410 in the lateral direction and inserts the accommodating unit 410 into the main body 100.

Accordingly, the drug container 10 is located inside the accommodating space 110, and the discharge port 14 communicates with the communication nozzle 120.

Here, the drug container 10 is fixed to a preset position on the accommodating unit 410 by the fixing means, so that the discharge port 14 can be located in a constant position even when the accommodating unit 410 is inserted into the main body 100.

In addition, since the drug container 10 is fixed to a constant position inside the accommodating space 110, the position of the communication nozzle 120 is also fixed and the discharge port 14 and the communication nozzle 120 are able to be stably connected to each other.

Thus, the drug container 10 can be easily installed inside the main body 100 by the sliding attachment unit 400, and can stably communicated with the insertion needle 200 so that the drug solution can be injected into the human body via the insertion needle 200.

Meanwhile, the solution injecting unit 500 is provided in the main body 100 to allow the drug solution accommodated in the drug container 10 to be injected into the human body via the insertion needle 200 due to the action of a user.

Specifically, the solution injecting unit 500 may mainly include a rotating shaft 510, a pressing member 520, and a driving motor 530. The rotating shaft 510 is formed to be long in the front and rear direction, and a screw thread 512 is formed on the outer surface of the rotating shaft 510.

The rotating shaft 510 is rotatably coupled to the main body 100 and is selectively rotated due to the action of a user.

The pressing member 520 slides forward and backward on the main body 100 to discharge the drug accommodated in the drug container 10.

Here, the pressing member 520 is penetrated by the rotating shaft 510 and is formed to be fitted to the screw thread 512. In addition, the position of the pressing member 520 is adjusted along the longitudinal direction of the rotating shaft 510 according to the rotating state of the rotating shaft 510.

As the pressing member 520 slides, the piston 12 provided in the drug container 10 is pressurized and the drug accommodated in the drug container 10 is discharged. In the present embodiment, the pressing member 520 is formed to be long and is bent at one end portion thereof in an upward direction, and comes into contact with the rear of the piston 12 formed in the drug container 10.

As the pressing member 520 slides forward, the pressing member 520 presses the piston 12 and the drug accommodated in the drug container 10 is discharged through the discharge port 14.

Meanwhile, the driving motor 530 is connected to the rotating shaft 510 and is driven by a separate operating means (not shown) to rotate the rotating shaft 510.

Specifically, the operating means is exposed to the outside of the main body 100 and is electrically connected to the driving motor 530, and the user operates the operating means to drive the driving motor 530.

Accordingly, the rotating shaft 510 is rotated by the rotation of the driving motor 530 to move the pressing member 520 forward.

Here, when the driving motor 530 is operated by the operating means, the driving motor 530 may be configured to rotate by a preset number of rotations when user operates the operating means once. Thus, the amount of the drug solution which is injected into the human body by the pressing member 520 can be controlled by the adjustment of the number of rotations of the driving motor 530.

Although not shown in the drawing, the driving motor 530 according to the present invention may be configured to rotate by a preset number of rotations when being operated by the operating means using a separate encoder or the like. Alternatively, various types may be applied.

Next, the configuration of the image measuring unit 300 will be described in more detail with reference to FIG. 6.

Figure 6:
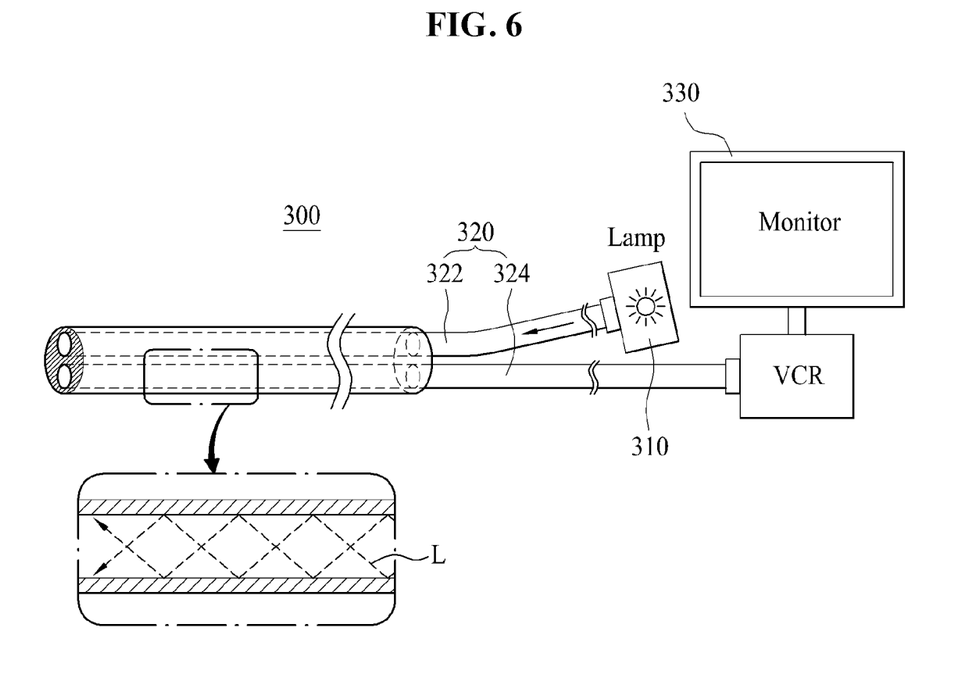
FIG. 6 is a view illustrating an operation state of a light emitting line and a photographing line of an image measuring unit in the drug injecting implement equipped with a sliding attachment unit of FIG. 1.

FIG. 6 is a view illustrating an operation state of a light emitting line and a photographing line of the image measuring unit 300 in the drug injecting implement equipped with a sliding attachment unit of FIG. 1

As shown, A part of the photographing unit 320 formed long along the longitudinal direction is formed of an optical fiber and includes the light emitting line 322 and the photographing line 324. Each line is formed long and the whole line can be inserted into the inside of the insertion needle 200 through the adapter 230.

The light emitting line 322 is connected to the light source 310 and receives and transmits light. One side of the light emitting line 322 is connected to the light source 310, and the received light is emitted from an end portion of the other side of the light emitting line 322.

The photographing line 324 is formed similarly to the above mentioned light emitting line 322 and transmits an image of the inside of the human body to the display unit 330. Specifically, the photographing line 324 is formed to be long and the other side is disposed on the insertion needle 200, and one side is connected to the display unit 330 so that an image is captured while the photographing line 324 is inserted into the inside of the human body and the captured image is transmitted to the display unit 330.

Here, each of the light emitting line 322 and the photographing line 324 are formed of a plurality of optical fiber bundles and, as shown in the drawing, transmit a light L through total internal reflection of the light L.

Thus, the image measuring unit 300 includes the light emitting line 322 and the photographing line 324 so that light can be supplied to the inside of the human body and the image inside the human body can be transmitted to an external apparatus.

As described above, the image measuring unit 300 includes the light emitting line 322 and the photographing line 324 formed of optical fiber bundles, and the light generated from the light source 310 can be emitted to the inside of the human body through the respective lines, and an internal image of the human body can be captured by the transmitted light, and the captured image can be transmitted to the display unit 330. Accordingly, the user can determine the position of the insertion needle 200 inside the human body and administer the drug solution to a desired position.

Next, a process of discharging the drug accommodated in the drug container 10 due to the action of a user will be described with reference to FIG. 7.

Figure 7:
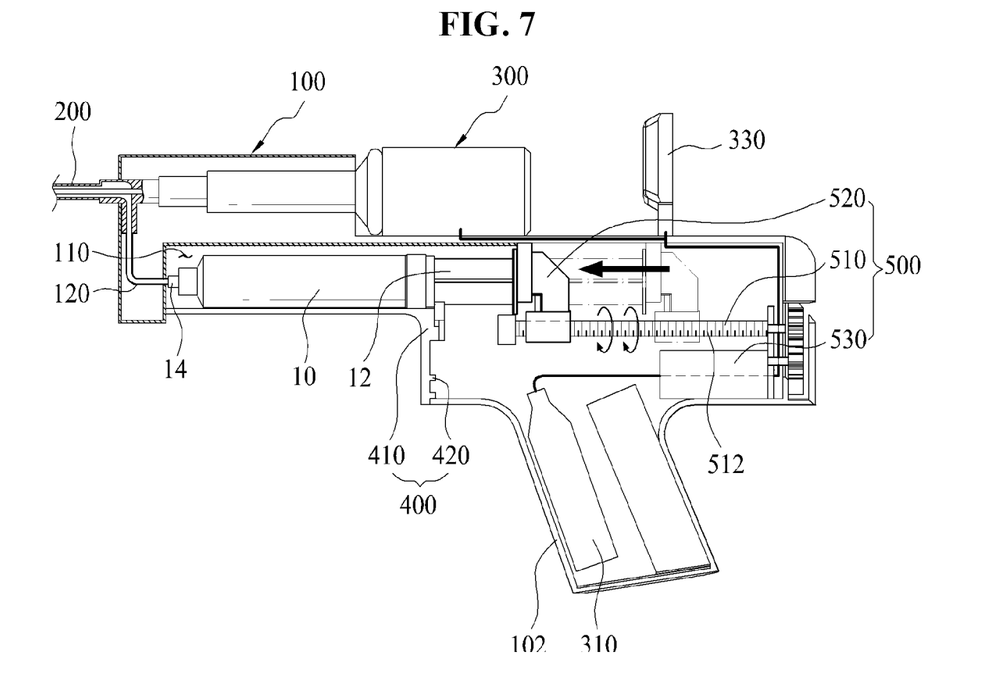
FIG. 7 is a view illustrating a state in which a drug is injected from the drug injecting implement equipped with a sliding attachment unit of FIG. 1.

FIG. 7 is a view illustrating a state in which a drug is injected from the drug injecting implement equipped with a sliding attachment unit of FIG. 1.

Referring to the drawings, the drug container 10 is coupled to a drug injecting implement equipped with a sliding attachment unit according to the present invention.

Here, since the piston 12 is protruded to the right when the drug container 10 is coupled to the main body 100 by the sliding attachment unit 400, an interference between the pressing member 520 and the end portion of the piston 12 can be prevented by adjusting the initial position of the pressing member 520.

In the present embodiment, as shown in the drawing, the pressing member 520 is disposed to be in contact with the right end of the piston 12. At this time, the discharge port 14 is connected to the communication nozzle 120 to communicate with the insertion needle 200.

Accordingly, the discharge port 14 communicates with the solution injecting unit 210, and the drug solution can be moved by the solution injecting unit 210 and injected into the human body via the insertion needle 200.

In addition, when the user operates the operating means, the driving motor 530 is driven to rotate the rotating shaft 510, so that the pressing member 520 slides and pushes the piston 12.

The drug solution accommodated in the drug container 10 moves along the solution injecting unit 210 by the pressure of the piston 12 and is injected into the user's body via the insertion needle 200.

At this time, the user adjusts the end position of the insertion needle 200 to a target position by the image measuring unit 300 while the insertion needle 200 is inserted into the human body of the patient.

As described above, the drug injecting implement equipped with a sliding attachment unit according to the present invention can check and adjust the position of the end portion of the insertion needle 200 inside the human body of the patient through the image measuring unit 300, and can be combined with the drug container 10 such as a universally used syringe and can be injected into the human body.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims. Accordingly, the scope of the present invention is not construed as being limited to the described embodiments but is defined by the appended claims as well as equivalents thereto.

The invention claimed is:

1. A drug injecting implement equipped with a sliding attachment unit, the implement comprising:
    a main body which has an accommodating space formed on an inside thereof, and is equipped with a handle to be gripped by a user;
    an insertion needle in which a solution flow pathway is formed for a drug solution to flow therethrough, and of which one side is secured inside the main body while another side extends outside the main body so as to be inserted into a human body;
    an image measuring unit which is disposed on the main body, and of which one portion is formed in elongated fashion so as to be inserted into the human body together with the insertion needle so as to capture an image;
    a sliding attachment unit which has an open topped accommodating unit for accommodating a separate drug container on an inside thereof, and which slides selectively on a side surface of the main body so as to position the drug container inside the accommodating space; and
    a solution injecting unit which is provided on the main body and is adapted such that the drug solution accommodated inside the drug container is injected into the human body via the insertion needle due to an action of the user, wherein the accommodating unit includes a side surface of which a length is the same as or longer than a length of the drug container in a longitudinal direction, and the side surface of the accommodating unit is disposed at a side of the drug container when the drug container is accommodated on the inside of the accommodating unit.

2. The implement of claim 1, wherein the drug container is provided with a discharge port through which the drug solution is discharged and which is disposed in one side of the drug container, wherein the main body is provided with a communication nozzle which allows the discharge port to communicate with the insertion needle when the drug container is positioned in the accommodating space by the sliding attachment unit.

3. The implement of claim 2, wherein the sliding attachment unit further comprises a sliding guide which is formed on an outer surface of the sliding attachment unit so as to be slidable in a lateral direction without being detached from the main body.

4. The implement of claim 3, wherein the accommodating unit further comprises a fixing means which surrounds a part of the side surface of the drug container to prevent the drug container from moving unintentionally inside the accommodating unit.

5. The implement of claim 1, wherein the solution injecting unit comprises:

a rotating shaft which is elongated in a front and rear direction in the main body and which has a screw thread formed on an outer surface of the rotating shaft, and which selectively rotates according to the action of the user; and a pressing member which is penetrated by the rotating shaft and which is fitted to the screw thread, and which slides forward and backward in the main body due to a rotation of the rotating shaft to discharge the drug accommodated in the drug container.

6. The implement of claim 5, wherein the solution injecting unit further comprises a driving motor which is connected to the rotating shaft and which provides a rotational force to the rotating shaft by a separate operating means.

7. The implement of claim 1, wherein the image measuring unit comprises:

a light source which is provided in the main body to emit light;

a photographing unit which is elongated and is disposed inside the insertion needle, and which receives the light emitted from the light source and photographs an internal image of a human body; and a display unit which is provided outside the main body and which displays the image photographed by the photographing unit to the user.

8. The implement of claim 7, wherein the photographing unit comprises a light emitting line which is connected to the light source and which emits light in the inside of the human body and a photographing line which photographs the internal image of the human body to transmit to the display unit.

9. The implement of claim 8, wherein the light emitting line and the photographing line are provided with an optical fiber.

10. The implement of claim 7, wherein the light source is provided inside the handle of the main body.

* * * * *